United States Patent
Vinciguerra

(10) Patent No.: US 10,881,517 B2
(45) Date of Patent: Jan. 5, 2021

(54) SOFT TISSUE REPAIR USING A POROUS COATED IMPLANT

(71) Applicant: Encore Medical, L.P., Austin, TX (US)

(72) Inventor: John Vinciguerra, Austin, TX (US)

(73) Assignee: Encore Medical, LP, Austin, TX (US)

(*) Notice: Subject to any disclaimer, the term of this patent is extended or adjusted under 35 U.S.C. 154(b) by 281 days.

(21) Appl. No.: 15/793,843

(22) Filed: Oct. 25, 2017

(65) Prior Publication Data
US 2018/0042728 A1 Feb. 15, 2018

Related U.S. Application Data

(63) Continuation of application No. PCT/US2016/024708, filed on Mar. 29, 2016.

(60) Provisional application No. 62/155,313, filed on Apr. 30, 2015.

(51) Int. Cl.
| | | |
|---|---|---|
| *A61F 2/30* | (2006.01) | |
| *A61B 17/04* | (2006.01) | |
| *A61F 2/08* | (2006.01) | |
| *A61F 2/28* | (2006.01) | |
| *A61L 27/06* | (2006.01) | |
| *A61B 17/00* | (2006.01) | |
| *A61B 17/16* | (2006.01) | |
| *A61B 17/80* | (2006.01) | |

(52) U.S. Cl.
CPC ...... *A61F 2/30767* (2013.01); *A61B 17/0401* (2013.01); *A61F 2/0811* (2013.01); *A61F 2/28* (2013.01); *A61L 27/06* (2013.01); *A61B 17/1659* (2013.01); *A61B 17/1684* (2013.01); *A61B 17/8061* (2013.01); *A61B 2017/00884* (2013.01); *A61B 2017/0404* (2013.01); *A61B 2017/044* (2013.01); *A61F 2/30756* (2013.01); *A61F 2002/0888* (2013.01); *A61F 2002/30003* (2013.01); *A61F 2002/30004* (2013.01)

(58) Field of Classification Search
CPC ............... A61F 2/30756; A61F 2/3872; A61F 2002/30761; A61F 2002/30762; A61F 2002/30766
See application file for complete search history.

(56) References Cited

U.S. PATENT DOCUMENTS

| | | | |
|---|---|---|---|
| 4,244,689 A | 1/1981 | Ashman | |
| 4,439,152 A | 3/1984 | Small | |
| 9,642,891 B2* | 5/2017 | Hart | A61B 17/0401 |
| 2005/0159754 A1 | 7/2005 | Odrich | |
| 2006/0149266 A1* | 7/2006 | Cordasco | A61F 2/0811 606/76 |

(Continued)

OTHER PUBLICATIONS

International Search Report and Written Opinion dated Sep. 27, 2016 for PCT Application No. PCT/US16/24708.

*Primary Examiner* — Megan Y Wolf
(74) *Attorney, Agent, or Firm* — Veros Legal Solutions, LLP

(57) ABSTRACT

Embodiments of this application relate to the use of porous coating implants to repair soft tissue injuries. Implant frames are coated with a porous coating, such as a titanium porous coating, for example, on both the bone-facing and the soft tissue-facing sides of the implant. The implant may then be sandwiched between the bone and soft tissue so that the bone grows into one side, and the soft tissue grows into the other side.

17 Claims, 18 Drawing Sheets

(56) References Cited

U.S. PATENT DOCUMENTS

| | | | |
|---|---|---|---|
| 2009/0228104 A1* | 9/2009 | Strzepa | A61F 2/30756 623/14.12 |
| 2010/0161073 A1* | 6/2010 | Thomas | A61F 2/30756 623/23.5 |
| 2013/0110252 A1* | 5/2013 | Bake | A61F 2/30756 623/23.57 |
| 2013/0131699 A1 | 5/2013 | Jiang et al. | |
| 2016/0100932 A1* | 4/2016 | Kumar | A61F 2/0811 606/70 |

* cited by examiner

SOFT TISSUE REPAIR USING A POROUS COATED IMPLANT

CROSS-REFERENCE TO RELATED APPLICATIONS

This application is a continuation of International Application No. PCT/US2016/024708, filed Mar. 29, 2016, which claims the benefit of U.S. Provisional Application No. 62/155,313, filed Apr. 30, 2015. Each of the above-referenced patent applications is incorporated by reference in its entirety.

BACKGROUND OF THE INVENTION

Field of the Invention

This application relates to repair of soft tissue. More particularly, this application relates to a device and method for repairing soft tissue injuries, such as rotator cuff injuries, for example, using a porous coated implant.

Description of the Related Technology

Injuries to soft tissue are often repaired by suturing the soft tissue to bone. For example, injuries to the rotator cuff are often repaired by direct suturing of the cuff to the shoulder bone. Sutures are often used along with bone screws and/or bone anchors which are implanted into the bone, and used in cooperation with the sutures to hold the soft tissue against the bone.

After soft tissue repair procedures, patients are often immobilized for extended periods of time in order to prevent the repaired soft tissue construct from tearing away from the bone or becoming otherwise compromised. For example, in rotator cuff repair procedures, patients are often placed in a sling for three to six months—told during that time not to perform any activity using the repaired shoulder. However, in practice, patients are often non-compliant during the early healing phase and many soft tissue repairs fail during the early healing phase. Accordingly, improved methods and devices for soft tissue repair are needed.

SUMMARY

In a first embodiment, a method of attaching a soft tissue to bone is provided. The method may include forming a depression in the bone underneath the anatomical footprint of the soft tissue and positioning a porous coating implant within the depression. The method may further include compressing the soft tissue against the porous coating implant.

In a second embodiment, a method of attaching soft tissue to a bone is provided. The method may include inserting an anchor into the bone and lifting soft tissue away from the bone. A porous coating implant may be positioned on the bone surface underneath the anatomical footprint of the soft tissue. The method may further include stitching a suture to the soft tissue and tensioning the suture to compress the soft tissue against the porous coating implant. The tensioned suture may be attached to the inserted bone anchor.

In a third embodiment, a method of attaching soft tissue to a bone is provided. The method may include lifting the soft tissue away from the bone and inserting a first bone anchor into the bone underneath the anatomical footprint of the soft tissue. The method may further include positioning a porous coating implant on the bone surface underneath the anatomical footprint of the soft tissue and passing a suture from the first bone anchor through the soft tissue. A second bone anchor may be inserted into the bone, beyond the anatomical footprint of the soft tissue. The suture may be tensioned to compress the soft tissue against the porous coating implant and the bone, and the tensioned suture may be secured to the second bone anchor.

DETAILED DESCRIPTION OF CERTAIN INVENTIVE EMBODIMENTS

Embodiments of this application relate to the use of porous coating implants to repair soft tissue injuries. Implant frames are coated with a porous coating, such as a titanium porous coating, for example, on both the bone-facing and the soft tissue-facing sides of the implant. The implant may then be sandwiched between the bone and soft tissue so that the bone grows into one side, and the soft tissue grows into and adheres to the other side. This in growth provides a stable mechanical attachment mechanism between the bone and the soft tissue. The porous coating implants disclosed herein may be utilized in various different surgical procedures to repair soft tissue. They may be utilized in soft tissue repairs which avoided entirely the need for the use of sutures and/or knot tying within the surgical site. In addition, the porous coating implants disclosed herein may be used in conjunction with traditional soft tissue repair procedures in order to provide additional stability during the early healing phase after the procedure. As discussed above, the inventor has recognized that patients are often non-compliant during the early healing phase, which often results in inadvertent re-injury of the repaired site. Using the porous coating implants disclosed herein, additional stability and strength may be provided to the surgical site during the early healing phase, allowing for more freedom of movement and also assisting and accelerating the healing process overall.

Figure 1A:
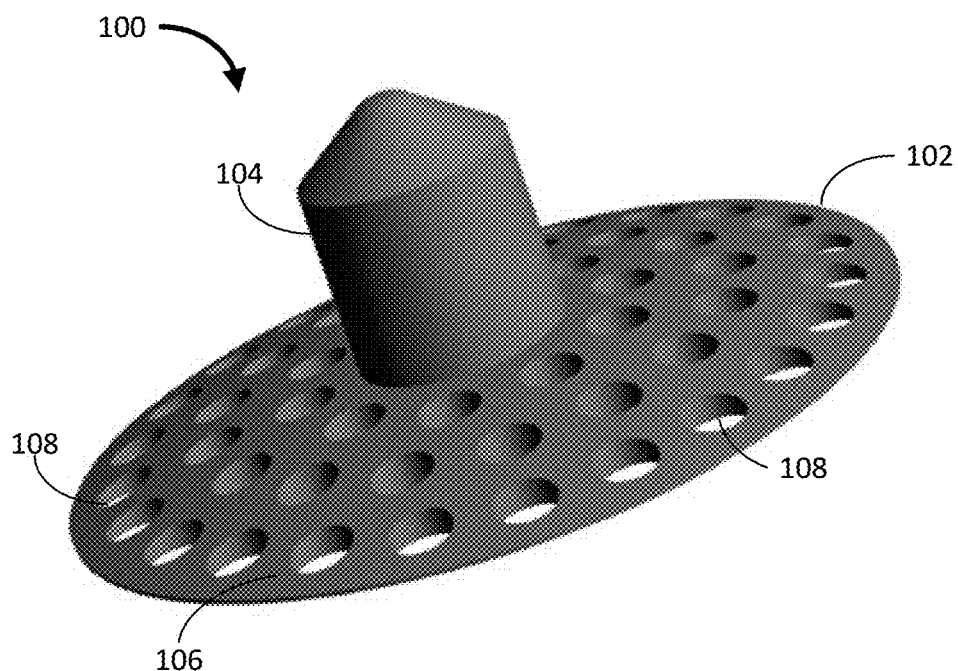
FIG. 1A is a perspective view of the bottom side of an uncoated implant frame according to one or more embodiments.

As is described below, the porous coating implants disclosed herein may take various forms, shapes, and frames. Depending on the particular embodiment, the implant may be circular, square, hexagonal, rectangular, or some other shape. FIG. 1A is a perspective view of the bottom side of a circular-shaped, uncoated implant frame 100 according to one or more embodiments. The implant frame 100 may include an implant body 102 and an implant stem 104 extending from the implant body 102. In use, the implant stem 104 may be inserted into a similarly sized aperture created in a patient's bone in order to secure the implant body 102 against the bone, or within a depression formed in the bone. The implant frame may be formed of any of various materials. For example, the implant frame 100 may be formed of a polymer such as peak, for example. The implant frame 100 may also be formed of a metal such as titanium, or some other metal suitable for use in vivo. The implant frame 100 may be produced using conventional milling techniques, or alternatively, it may be produced using additive manufacturing techniques such as E-Beam melting (EBM), Direct Metal Laser Sintering (DMLS) or the like.

As shown in FIG. 1A, the implant body may include a bottom (inferior) surface 106. The bottom surface 106 may have a slight rounding or curvature such that it has a slightly convex shape from its outer edge toward the stem 104 which extends out of the bottom surface 106 of the implant body 102. The implant body 102 also include a plurality of apertures 108. The apertures 108 may extend through the implant body 102. In this particular example, the apertures 108 are circular shaped, but other shapes may be used. The shapes of the apertures may be oval, elliptical, square, rectangular, hexagonal, octagonal, or some other shape. The apertures 100 may generally allow the porous coating to permeate the implant frame 100 as will be discussed in detail below.

Figure 1B:
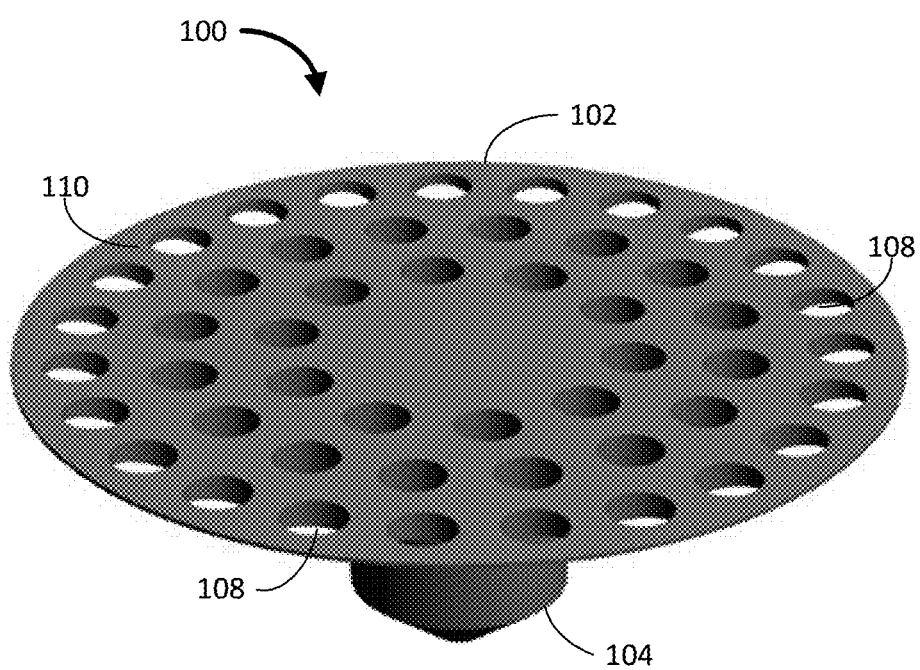
FIG. 1B is an elevated perspective view of the uncoated implant frame from FIG. 1A.

FIG. 1B is an elevated perspective view of the top (or superior) side of the uncoated implant frame 100 from FIG. 1A. As shown, the uncoated implant frame 100 includes a top (superior) surface 110. In this example, the top surface 110 is relatively flat (unlike the bottom surface 106 which has a slightly convex curvature as discussed above in connection with FIG. 1A). However, it is to be appreciated that the top surface 110 not necessarily be a flat surface, and it can also be curved or uneven in some other respect. As noted above, the apertures 108 extend through the body frame 102 from the bottom surface 106 to the top surface 110 as shown in FIG. 1B.

Figure 1C:
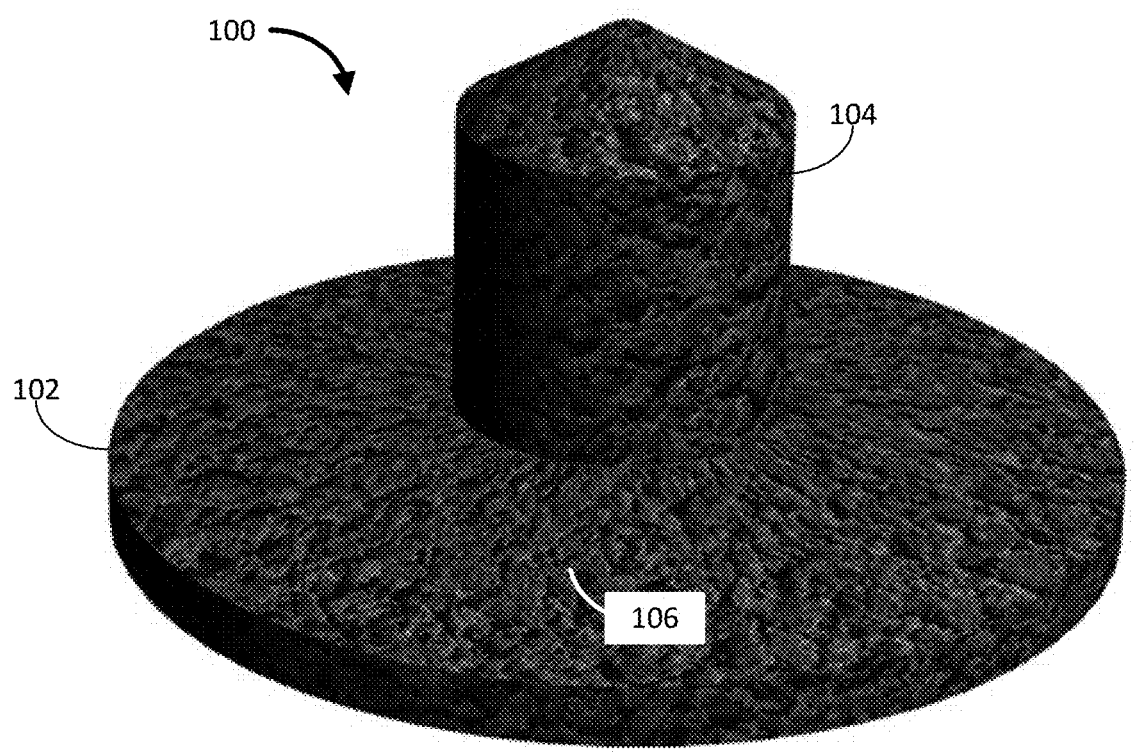
FIG. 1C is a perspective view of the bottom side of the implant frame from FIG. 1A with a porous coating applied.

As noted above, embodiments of the invention involve utilizing an implanted device having a porous coating to promote bone in growth and tissue attachment in connection with soft tissue repair procedures. FIG. 1C is a perspective view of the bottom side of the implant frame from FIG. 1A with a porous coating applied. In various embodiments disclosed herein, the porous coating may have two distinct pore sizes. The porous coating may include a first pore size which promotes fixation with bone. The porous coating may also include a second pore size which promotes soft tissue attachment. Thus, using a porous coating with two different pore sizes allows both the bone and soft tissue grow into the coating.

In this particular embodiment, the coated implant frame 100 is completely covered in a porous coating. Shown in FIG. 1C, the bottom (inferior) surface 106 of the implant body 102 is completely coated in a porous coating, the coating extending through and around the apertures 108 (not shown due to the coating) so that the entire exterior surface of the implant body 102 is coated. Additionally, in this particular example, the implant stem 104 is also coated. By providing a coating over the stem 104, bone in growth is further promoted, and the implant stem 104 can provide increased stability. However, it is to be appreciated that the stem 104 may also be left without a coating which may provide for an improved removal capability if needed.

Figure 1D:
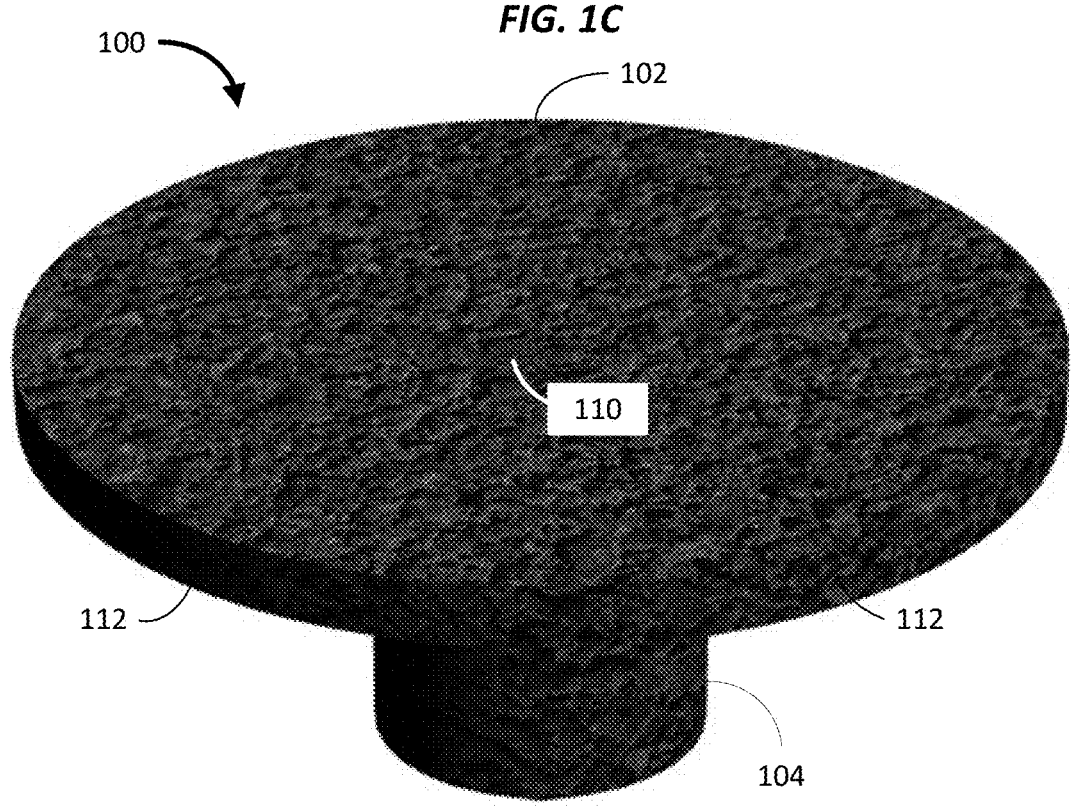
FIG. 1D is an elevated perspective view of the implant frame from FIG. 1A after application of a porous coating.

FIG. 1D is an elevated perspective view of the implant frame from FIG. 1A after application of a porous coating. As shown, the coating has been applied to the top surface 110, and the coating of the bottom surface 106 and the top surface 110 collectively bond to form a side surface 112 having a thickness substantially greater than the edge of the uncoated implant frame 100.

Figure 1E:
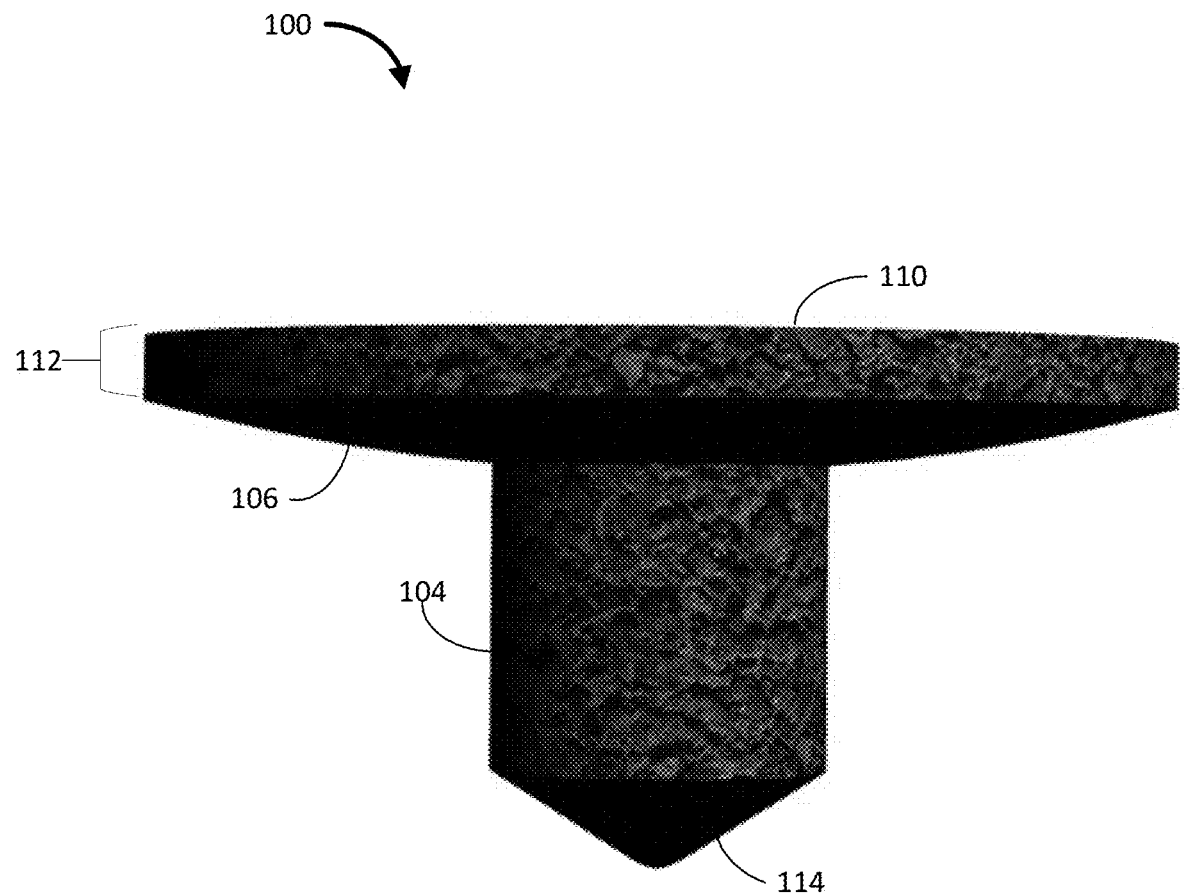
FIG. 1E is a side view of the coated implant frame.

FIG. 1E is a side view of the coated implant frame. As shown, the coating applied to the implant frame 100 may have a thickness as a result of the thickness of its application, thereby creating side surface 112 which has a substantially uniform thickness around the circular shape of the implant body 102. As shown in FIG. 1E, the coated bottom surface has a slightly convex curvature (as noted above). Additionally, the coated stem portion 104 of the implant frame 100 may also include a tapered inferior end 114. The tapered inferior end 114 may be coated, although in some embodiments it may be left without coating in order to improve its ability to be driven into the bone.

Figure 2A:
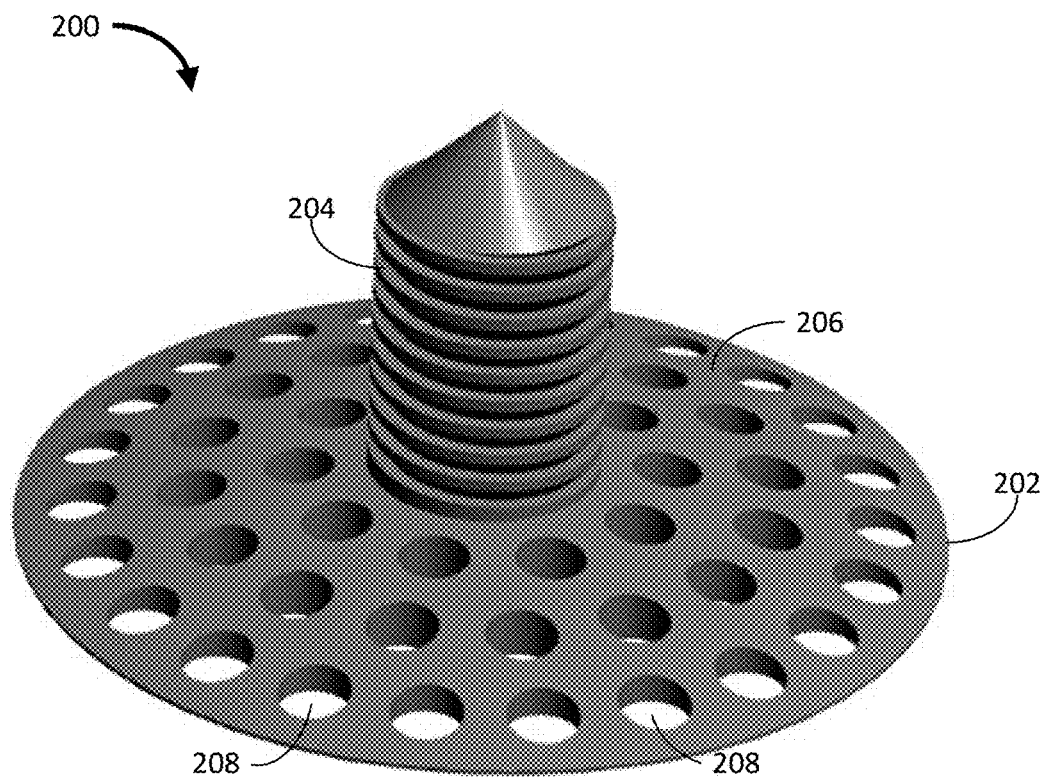
FIG. 2A is a perspective view of the bottom side of an uncoated implant frame having a threaded stem.

In some embodiments, the implant may include a threaded stem which allows it to be secured within the bone by rotating the implant to drive the threaded stem into the bone. FIGS. 2A-2E provide an example of an implant with a threaded stem. FIG. 2A is a perspective view of the bottom side of an uncoated implant frame 200 having a threaded stem. As shown, the uncoated implant frame 200 includes an implant body 202 and an implant stem 204 extending inferiorly to a tapered inferior end 214 (shown in FIG. 2E). The implant stem 204 is threaded, as noted above Like the previous embodiment, the implant body may include a plurality of apertures 208 which extend from the inferior surface 206 through the body out to the top surface 210 (shown in FIG. 2B).

Figure 2B:
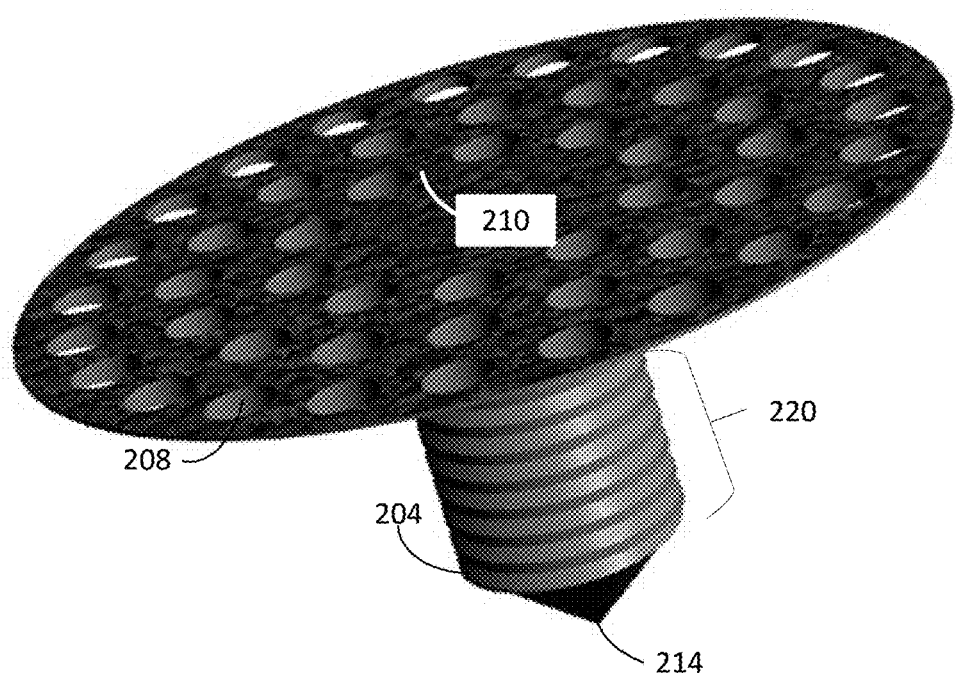
FIG. 2B is an elevated perspective view of the threaded-stem implant frame from FIG. 2A.

FIG. 2B is an elevated perspective view of the threaded-stem implant frame from FIG. 2A. from this view, the top (superior) surface 210 of the implant 200 is prominently featured. Moreover, the apertures 208 are shown extending into the top surface 210. As with the previous embodiment, the top surface in this example is substantially flat, while the inferior surface has a convex curvature which may be better suited to conform to a surface of the bone that has been prepared using a reamer (as will be discussed in more detail below). Also shown in FIG. 2B are a plurality of threads 220 which are present on the threaded stem 204.

Figure 2C:
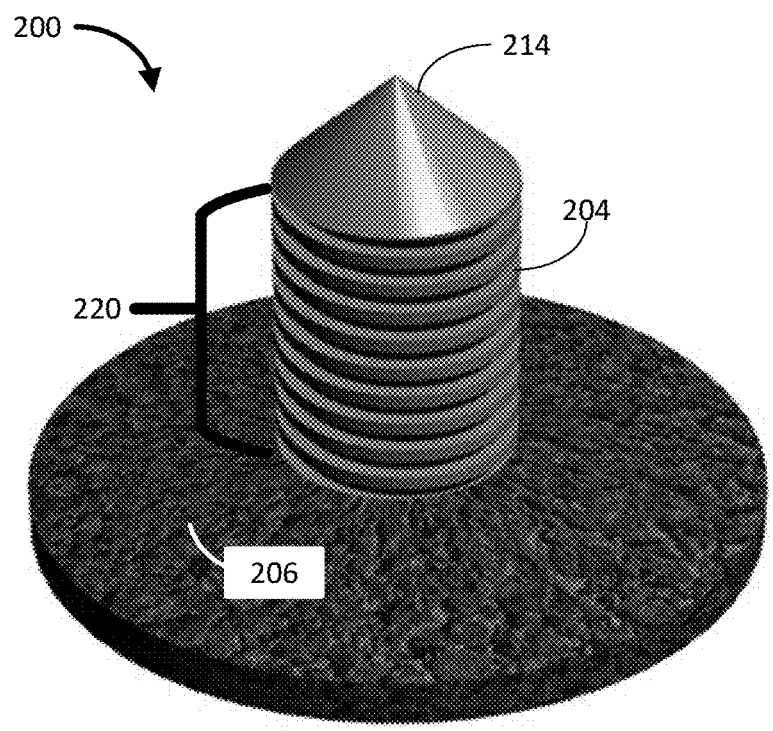
FIG. 2C is a perspective view of the bottom side of the implant frame from FIG. 2A with a porous coating applied.

A porous coating may be applied to the implant frame 200 shown in FIGS. 2A-2B. However, unlike the embodiment shown in FIG. 1, the coating may be applied only to the implant body 202 and not to the implant stem 204. The porous coating is not applied to the implant stem 204 because the implant stem 204 includes the threads 220 which are used to secure the implant within the bone. FIG. 2C is a perspective view of the bottom side of the implant frame from FIG. 2A with a porous coating applied. As shown in FIG. 2C, the bottom (inferior) surface 206 of the implant 200 has been coated with an applied porous coating. The implant stem 204 and its associated threads 220 are not coated. In some embodiments, a female hex geometry may be provided in the center of the top surface 210 which allows a hex driving tool to easily rotate the implant stem 204 and its associated threads 220 into the bone.

Figure 2D:
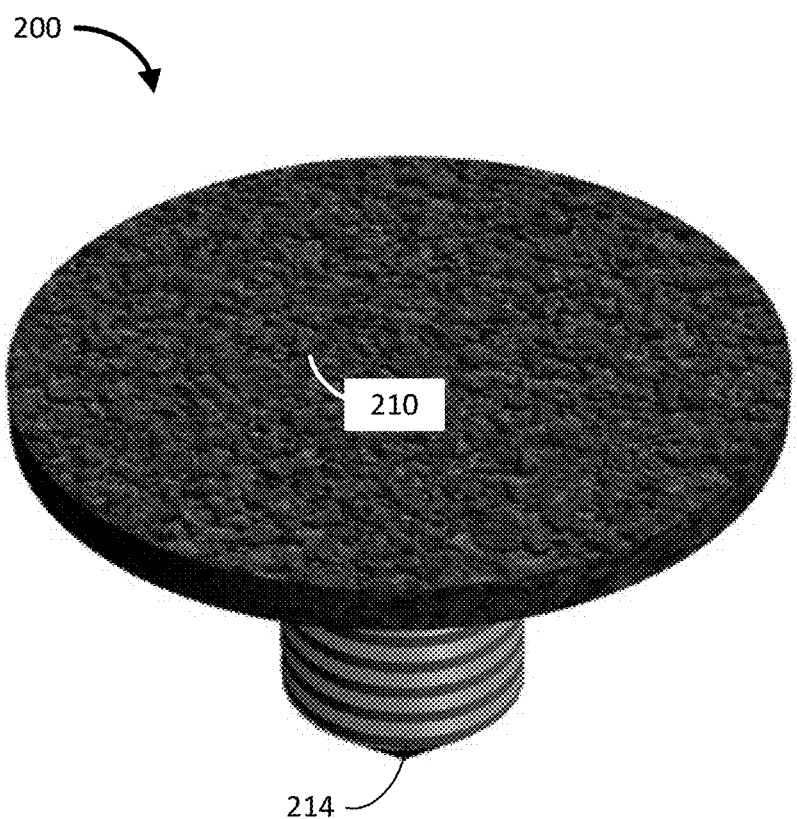
FIG. 2D is an elevated perspective view of the coded implant frame from FIG. 2A.
Figure 2E:
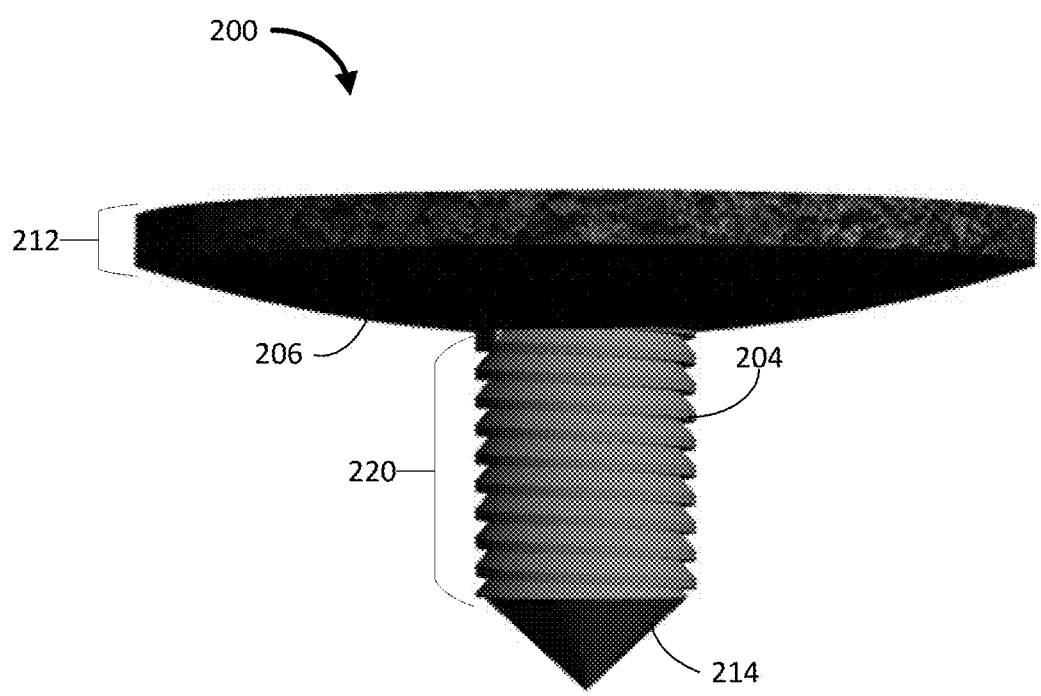
FIG. 2E is a side view of the coated, threaded-stem implant frame.

FIG. 2D provides an elevated perspective view of the top surface of the implant frame 200 with the porous coating applied. As shown, the porous coating permeates through the apertures 208 and creates a layer of material over both the bottom (inferior) surface 206 and the top (superior) surface 210 imparting the implant body with a side surface 212 as shown in FIG. 2E.

In some embodiments, the implant may be stemless. In these configurations, a shallow depression may be formed in the bone underneath the soft tissue, and implant may be placed in the depression so that the bone integrates with the porous coating on the inferior surface of the implant. Similarly, the soft tissue may bond and integrate with the porous coating on the superior surface of the implant. In these embodiments, the preparation of the bone is especially easy, as it requires only reaming of a shallow depression in the surface of the bone which is sized to receive the implant. The shallow depression may be of a depth that is substantially similar to the depth of the side surface of the implant after the coating has been applied.

Figure 3A:
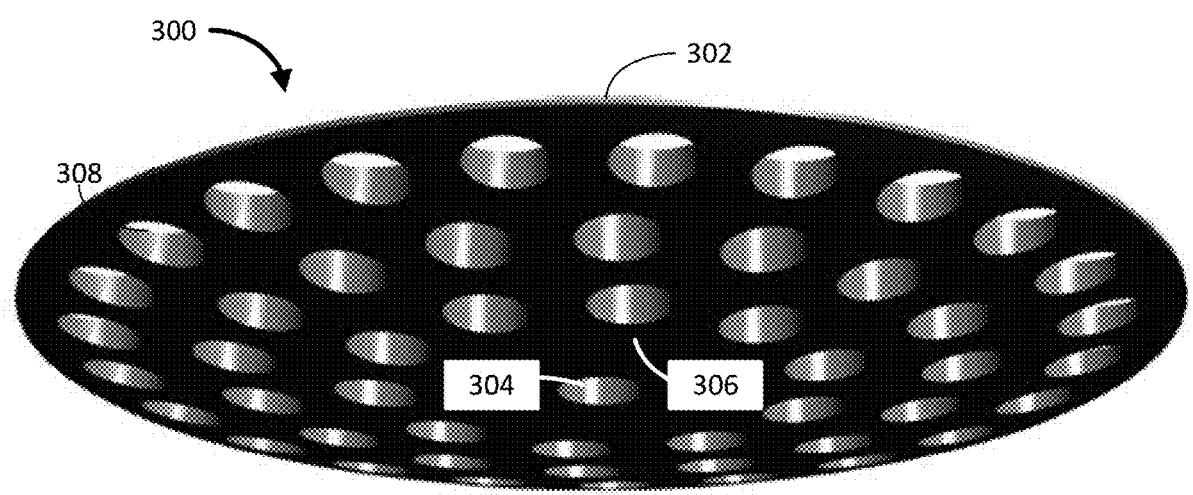
FIG. 3A is a perspective view of the bottom side of a stemless implant frame according to one or more embodiments.

FIGS. 3A-3E provide one example of a stemless implant. Referring specifically to FIG. 3A, a perspective view of the bottom side of a stemless implant frame 300 is shown. The stemless implant frame 300 includes a body 302. The implant frame 300 also includes a center portion 304, which in this example, includes a center aperture. In the example shown in FIG. 3A, the bottom (inferior) surface 306 of the implant frame is shown, with a plurality of apertures 308 arranged in increasingly small concentric circles moving inward towards the center aperture. A skilled artisan will appreciate that the apertures may have different shapes, and a different arrangement on the frame in accordance with other embodiments.

Figure 3B:
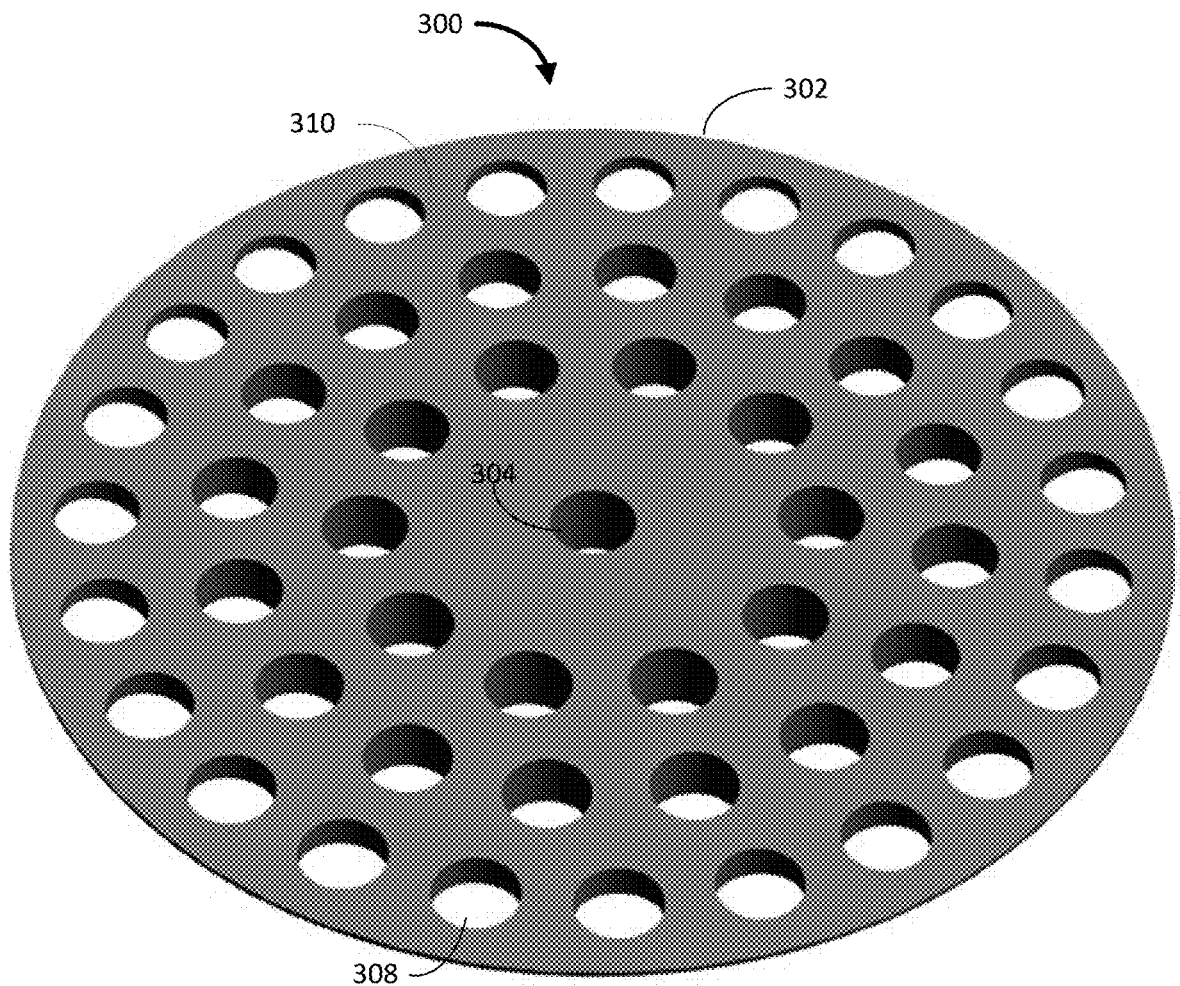
FIG. 3B is an elevated perspective view of the stemless implant frame from FIG. 3A.
Figure 3C:
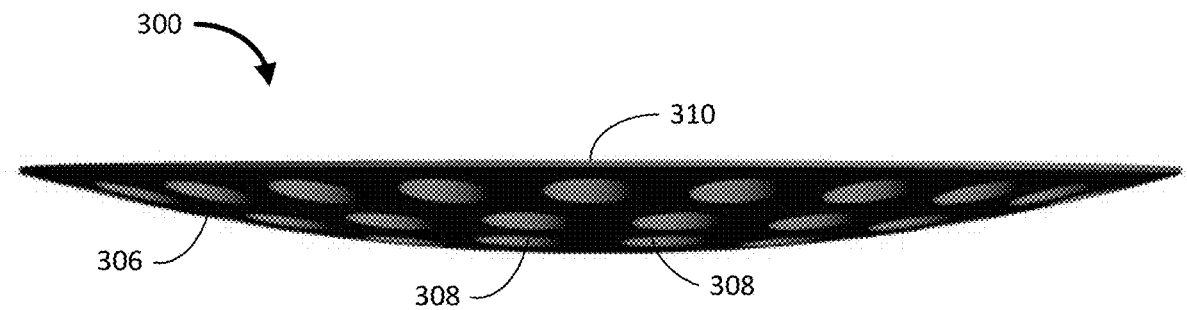
FIG. 3C is a side view of the uncoated implant frame from FIG. 3A.

Turning now to FIG. 3B, an elevated perspective view of the top of the implant frame 300 is shown. As shown, the implant frame includes a top (superior) surface 310, and the apertures 308, including the aperture in center portion 304, are shown extending through from the bottom (inferior) surface 306 to the top (superior) surface 310. FIG. 3C is a side view of the implant frame 300 from FIG. 3A. The implant frame 300 has a flat top surface 310, while the bottom surface 306 is a slight curvature such that the width of the frame 300 is slightly greater in the center portion 304 then at the outer edges of the circular disk.

Figure 3D:
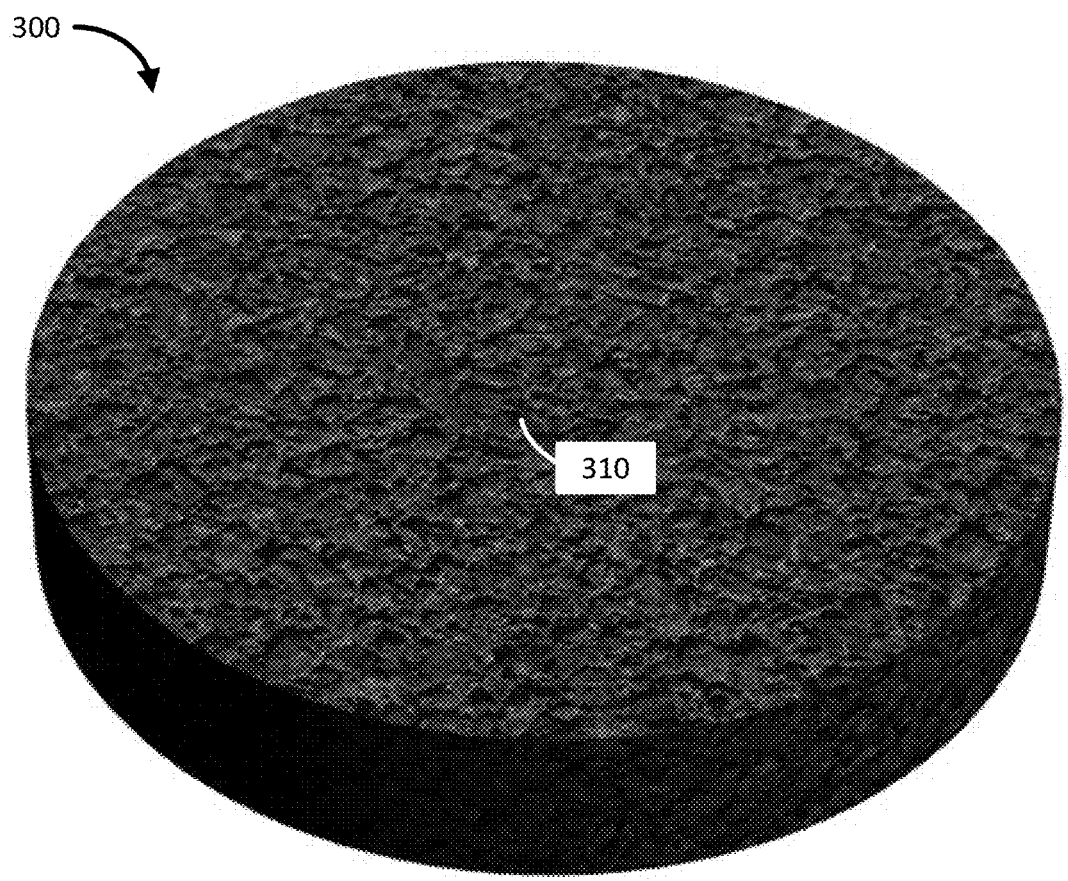
FIG. 3D is an elevated perspective view of the stemless implant frame from FIG. 3A with a porous coating applied.
Figure 3E:
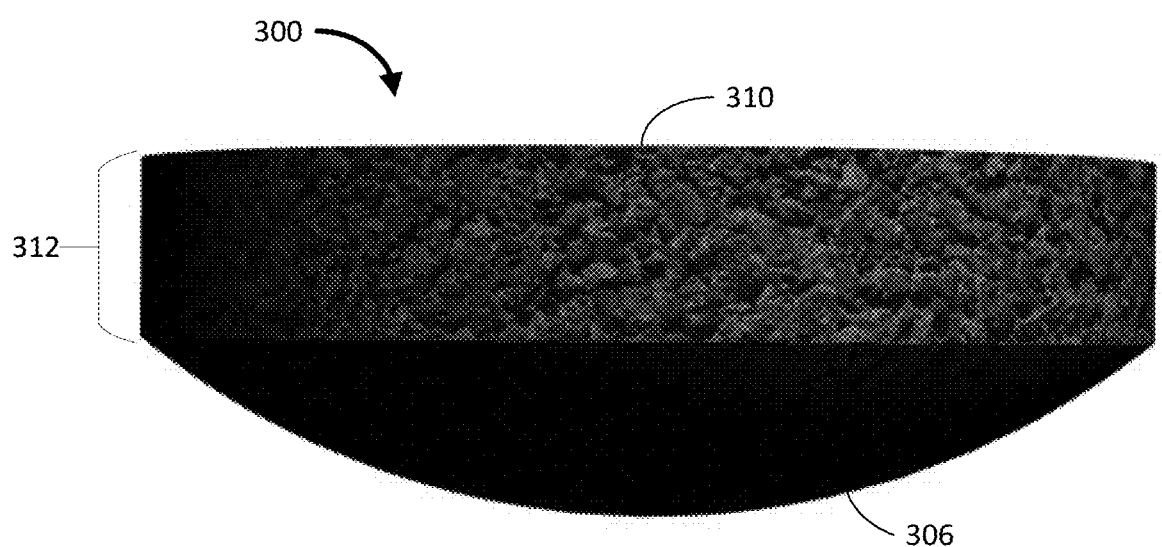
FIG. 3E is a side view of the coded implant shown in FIG. 3D.

As with other embodiments, the implant frame 300 may receive an applied porous coating which promotes bone ingrowth and soft tissue attachment. FIG. 3D is an elevated perspective view of the stemless implant frame from FIG. 3A with a porous coating applied. As shown, the coated implant 300 has a coated top surface 310 and a coated bottom surface 306. The application of the porous coating results in the implant frame 300 having a side surface 312 which is more easily viewed in FIG. 3E. As shown in FIG. 3, the side surface 312 has a relatively substantial thickness around the entire implant frame. In this particular example, the thickness of the side surface 312 is relatively uniform around the entire implant frame 300. However, a skilled artisan will appreciate that in some embodiments, the side surface may have an irregular width, being thicker in some areas and thinner in others. The side view of the coated implant shown in FIG. 3E also provides a view of the convex shape of the bottom (inferior) surface 306. As noted above in connection with the earlier disclosed embodiments, this convex shape may be utilized to substantially conform to a depression created in the bone using a reamer or other surgical tool. In some embodiments, the bottom surface may have a flat shape, or even a concave shape.

Figure 4A:
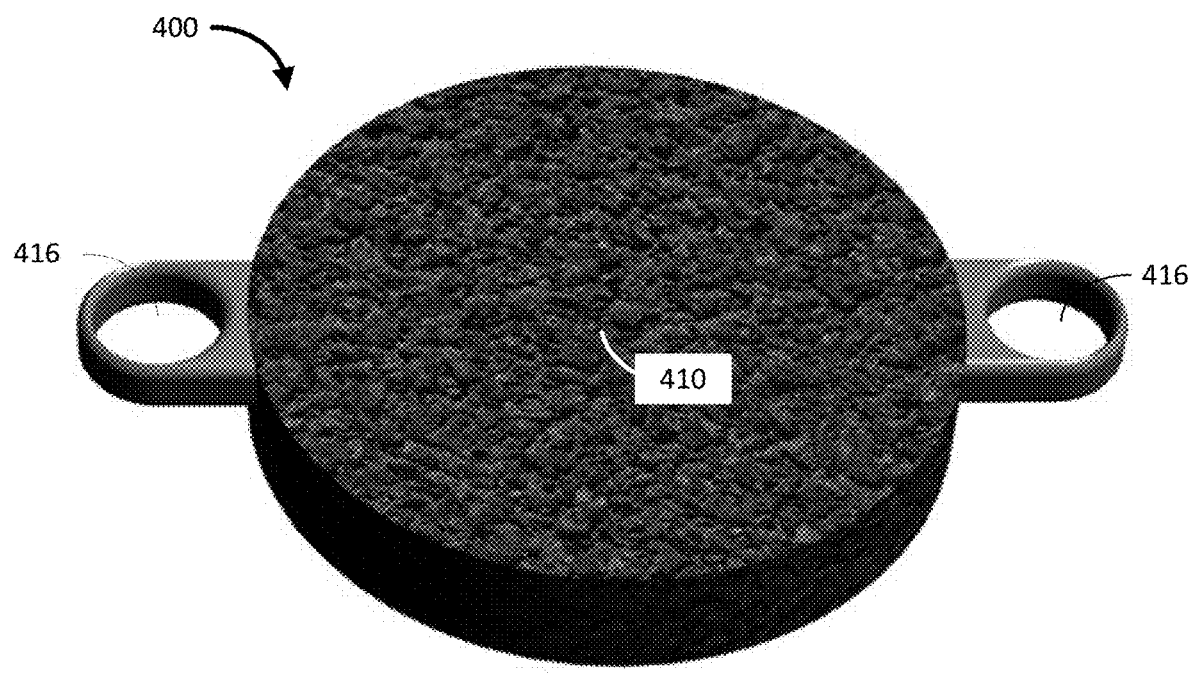
FIG. 4A is an example of a circular, porous coating implant having two eyelets according to one or more embodiments.
Figure 4B:
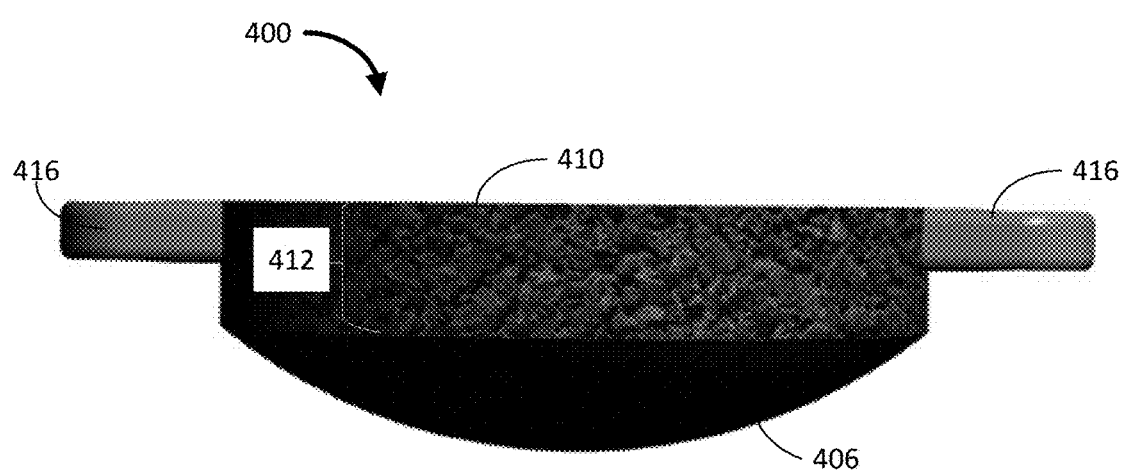
FIG. 4B is a side view of the porous coating implant shown in FIG. 4A.

In some embodiments, a stemless porous coating implant may be provided with additional features which improve stability and fixation prior to bone integration. FIGS. 4A-4B provide an example of an implant that has fixation features in the form of two eyelets. With specific reference to FIG. 4A an example of a circular, porous coating implant having two eyelets is provided. As shown, this implant 400 has a porous coating over an implant frame similar to that shown in FIG. 3A. However, the implant frame further includes two eyelets 416 to which a porous coating has not been applied. These two eyelets 416 may receive fixation devices such as bone screws, bone anchors, or bone nails, which may affix the implant 400 to the bone thereby preventing any migration of the implant 400 during the healing phase. FIG. 4B is a side view of the porous coating implant shown in FIG. 4A. As shown, the eyelets 416 extends from two sides of the implant 400, in this example diametrically opposed sides. In this particular example, the eyelets 416 have a thickness which is less than the thickness of the side surface 412 of the coated implant. Although the eyelets 416 may have a thickness greater than, less than, or the same as the side surface 412, in this embodiment, the reduced thickness may allow the implant to be further recessed into the bone. In cases where the eyelets 416 have a thickness greater or the same as the side surface 412, a reamed depression may not be needed. Instead, the implant may sit proud of the bone, and the bone may be roughened with a burr prior to placing the implant. Increasing the surface roughness prior to placement of the implant may promote bone in-growth. and suturing through the eyelets may secure the implant to the bone. Moreover, in some embodiments the eyelets may be positioned differently around the circumference of the circular shape of the implant 400, and are not necessarily diametrically opposed.

In the embodiments disclosed in FIGS. 1-4, the porous coating implants had generally circular shapes and profiles.

Figure 5A:
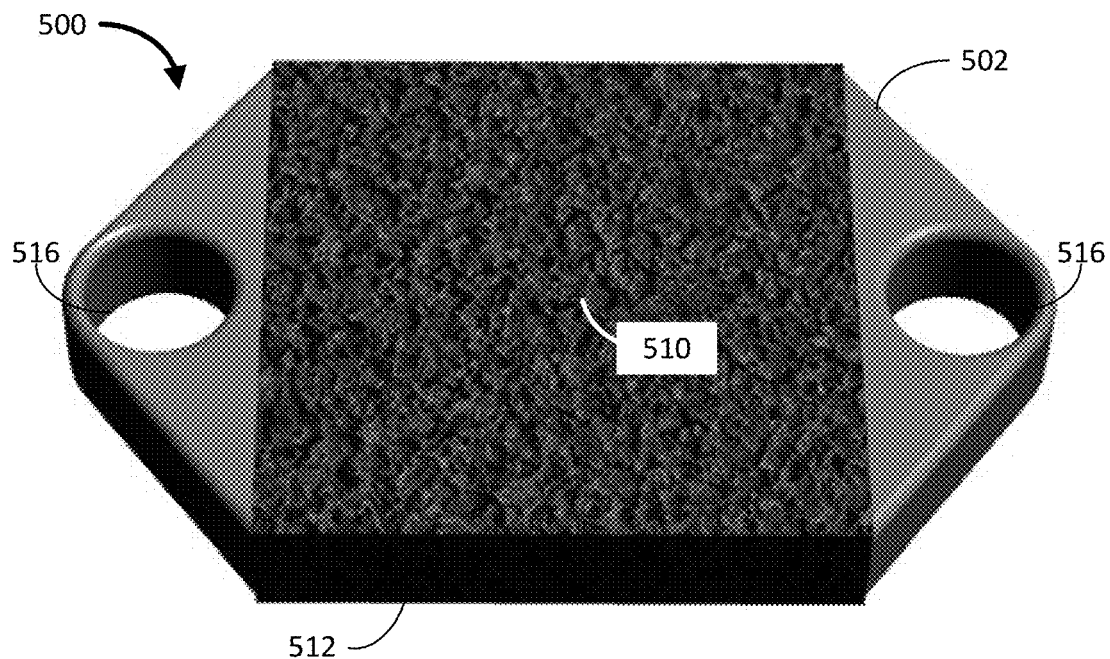
FIG. 5A an example of an implant with a square coating area and two eyelets according to one or more embodiments.

In some embodiments, however, the implants may take different shapes. FIG. 5A an example of an implant frame 500 with a square coating area and two triangular-shaped eyelets. As shown in FIG. 5A, a porous coating may be applied to the square coating area resulting in a coated top surface 510 and a coated bottom surface 506 (shown in FIG. 5B). The triangular-shaped eyelets areas on the frame 500 remain uncoated. In these non-circular embodiments, a circular reamer may be used to create the depression (which is a circular shape). After the implant is placed within the depression, the remaining circumferential areas may be packed with bone paste from the reamer. Alternatively, a a reamer with a flat end-cutting feature (non-convex) may also be used to create an appropriately-shaped depression. [

Figure 5B:
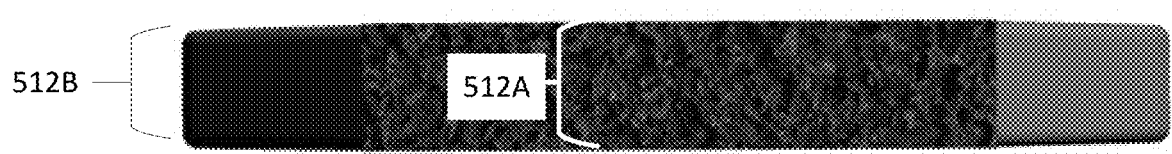
FIG. 5B is a side view of the implant shown in FIG. 5A.

FIG. 5B is a side view of the implant shown in FIG. 5A. As shown, the coated implant 500 has a porous coating side surface 512A which is contiguous with the square coating area. The coated implant 500 also includes one or more smooth side surfaces 512B which form the external surface surrounding the triangular eyelet portion of the implant 500.

Figure 6A:
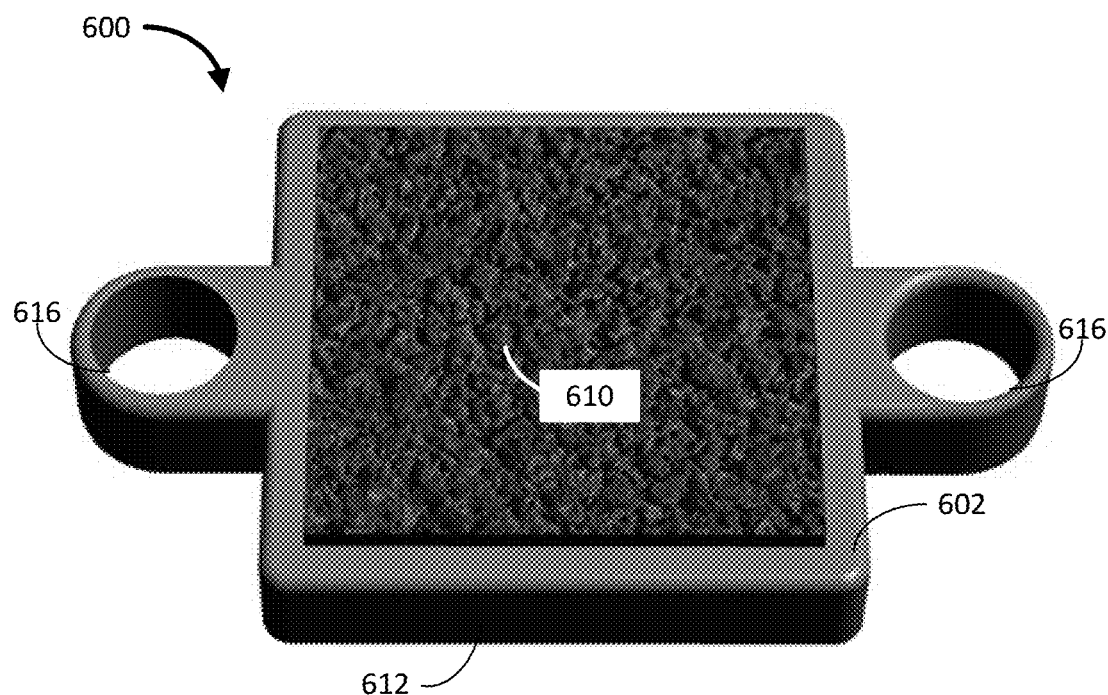
FIG. 6A is an elevated perspective view of a square-shaped porous coating implant with two eyelets according to one or more embodiments.
Figure 6B:
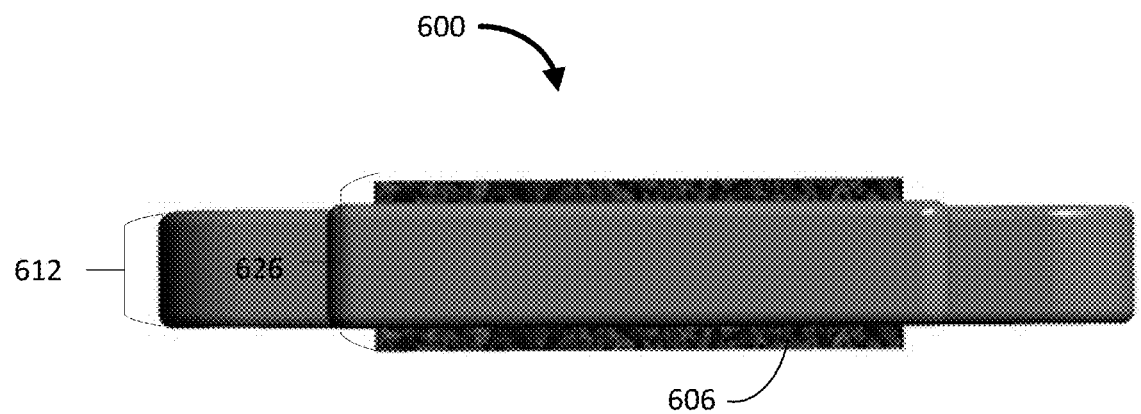
FIG. 6B is a side view of the implant shown in FIG. 6A.

Turning now to FIG. 6A, another example of an implant with two eyelets is provided. As shown, an implant frame 600 generally includes a square coating portion 610 within a square frame 602 which includes into eyelet portions 616 extending from the square coating portion. As with previous embodiments having eyelets, the eyelets 616 may be configured to receive fixating devices such as screws, bone anchors, sutures, nails, or any combination thereof, which provide secure fixation of the implant to the bone. FIG. 6B provides a side view of the implant shown in FIG. 6A. in this particular example, coated portion of the implant has a thickness 626 which is slightly larger than the thickness 612 of the implant frame 600. As can be seen from the figure, the coated portion extends upwardly beyond the boundary of the frame 600, and it also extends downwardly in a similar fashion. In this particular embodiment, the eyelets 616 have the same thickness as the square frame 602, and may be used without forming a depression in the bone. Because the "full thickness" eyelet is designed to be placed on top of the bone and not recessed, extending the porous coating beyond the frame allows the porous coating to always be in contact with the bone.

Figure 7A:
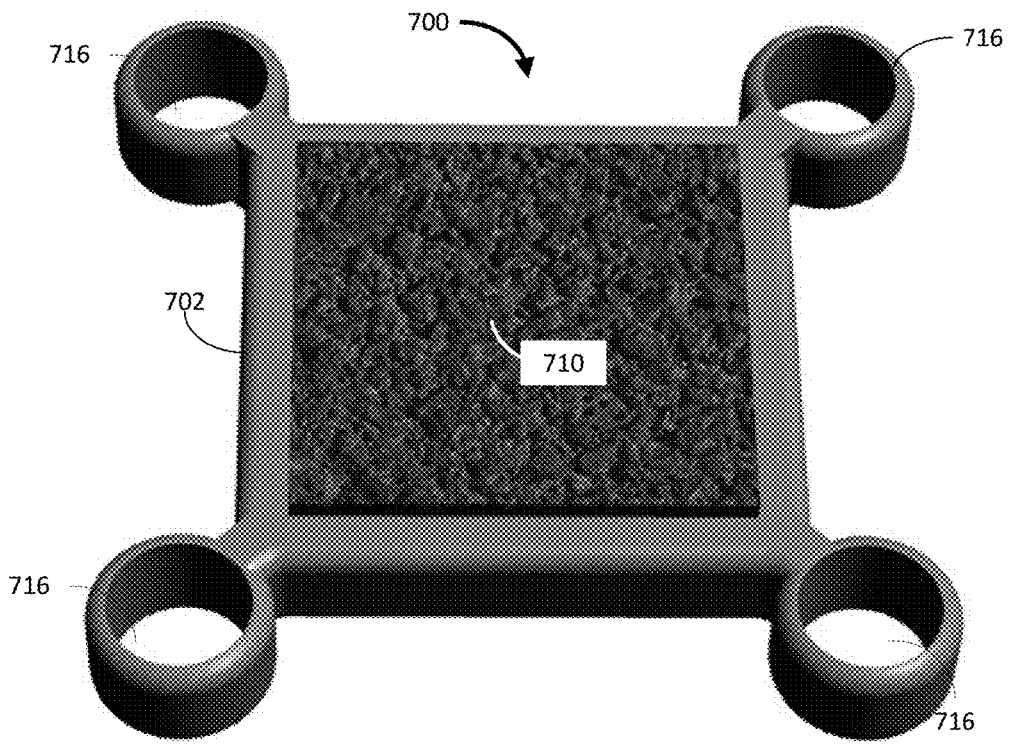
FIG. 7A is an elevated perspective view of a square-shaped porous coating implant with four eyelets according to one or more embodiments.
Figure 7B:
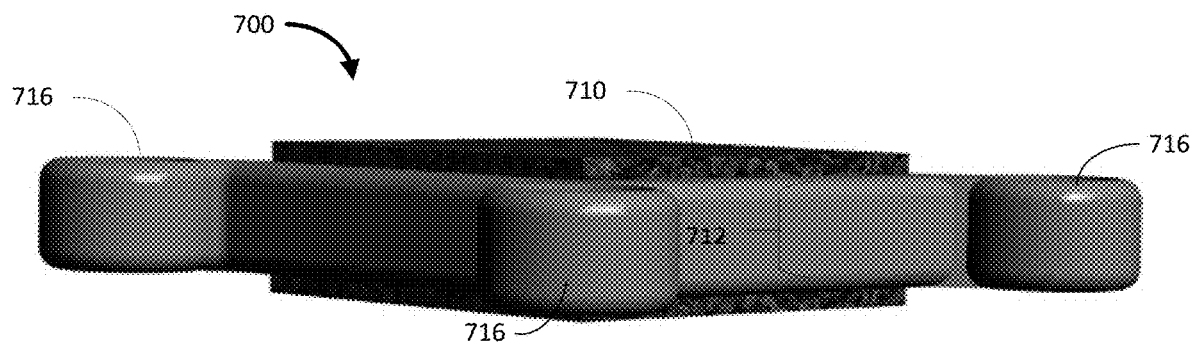
FIG. 7B is a side view of the implant shown in FIG. 7A.

Turning now to FIGS. 7A and 7B, another embodiment of an implant having eyelets is provided. In this case, the configuration is generally similar to that shown in FIGS. 6a-6B, but instead of having two eyelets extending from the center of the frame, in this embodiment each corner of the square-shaped frame includes an eyelet portion. With specific reference to FIG. 7A, an implant frame 700 with an applied coating is shown. The eyelet frame 700 includes a body portion 702 within which the porous coating is applied. Extending from the corners of the body portion 702 are eyelets 716. Each eyelet may receive a fixation device to secure it to the bone and/or the soft tissue of the patient. Turning to FIG. 7B, a side view of the implant frame is provided. As was the case with the previous embodiment discussed in connection with FIG. 6B, the coated portion may have a thickness which is somewhat greater than the thickness of the side surface 712 (including the eyelet portions 716) of the implant frame 700. This four-eyelet configuration may be especially useful to treatment of severe full-thickness tears.

Figure 8:
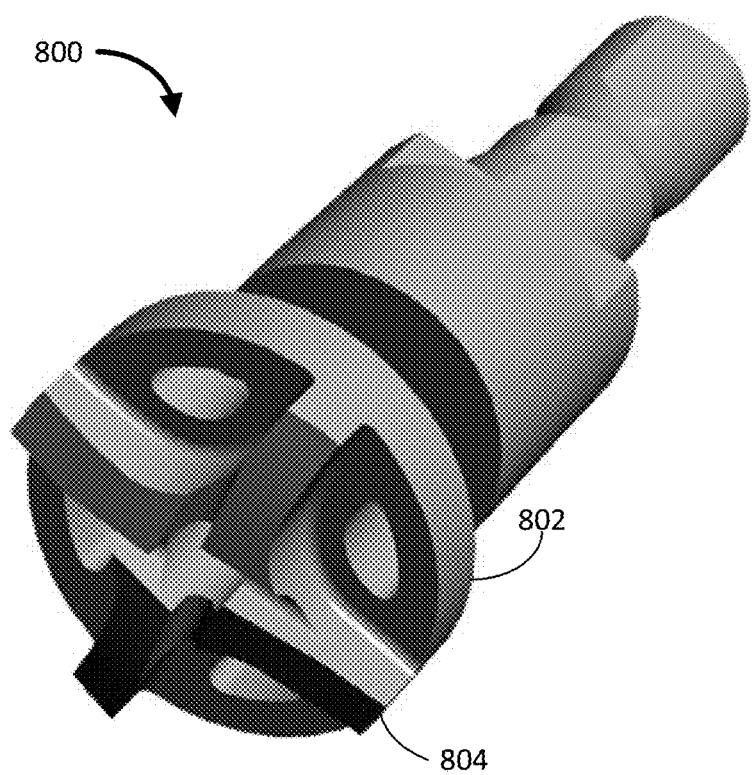
FIG. 8 is an example of a reamer which may be used to prepare a bone site four receiving any one or more of the implants shown in FIGS. 1-7 above.

Various embodiments may provide for placement of a porous coating implant within a depression formed in a bone of a patient. In some cases, the natural curvature of the bone may form a depression that may be used to position the implant. In some cases, the implant sits proud the bone, even if a natural depression is not formed. However, in many other cases, the depression may be created surgically. FIG. 8 provides an example of a reamer which may be used to prepare a bone site to receive any one or more of the implants shown in FIGS. 1-7 above. As shown, the reamer 800 may include a head 802 which is placed against the bone cut away bone material using fast rotational movement. The head has a cutting surface which includes cutting blades 804. The cutting blades 804 may each have a slight curvature so as to increase the depths of the reaming closer to the center of the head 802. This curvature allows the depression formed by the reamer to better conform to the convex bottom surface of the various implant embodiments described above.

Figure 9:
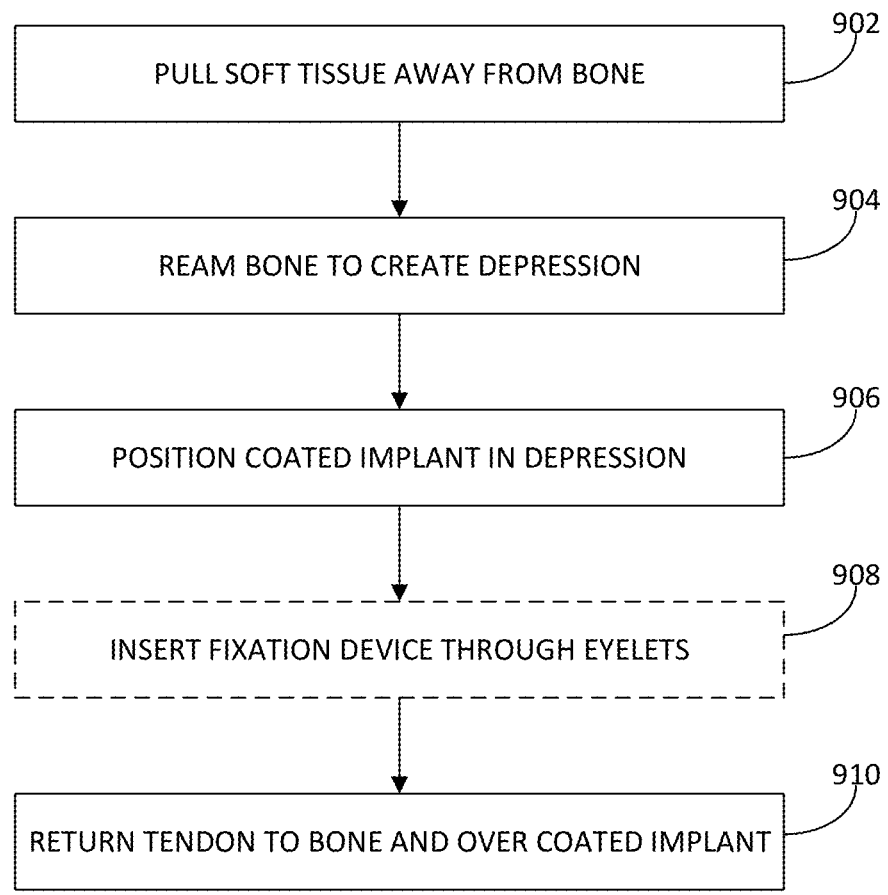
FIG. 9 is an example of a method of repairing soft tissue without needing sutures using a porous coating implant.

Using the porous coating implants described in FIGS. 1-7 above, various soft tissue repairs may be practiced according to embodiments of the inventions disclosed herein. For example, using the porous coating implants described above, a soft tissue repair may be achieved without the need for any sutures or bone anchors. FIG. 9 is an example of a method of repairing soft tissue without needing sutures using a porous coating implant. The method begins at block 902, where the injured soft tissue or tendon is pulled away from the bone in order to create access to the surgical site. Next, at block 904, the surface of the bone is reamed in order to create a slight depression in the bone surface. A reamer such as the reamer described in FIGS. 8A-8C may be used to create the depression. Or other surgical tools may be used instead. Next, the process moves to block 906. There a porous coating implant is positioned within the depression. Next, the process may move to an optional step 908. This step is optional, because it involves inserting fixation devices through any eyelets which are present on the frame of the implant. As noted previously, in several embodiments the implants may not include eyelets. As a result, the step described in block 908 may not been necessary in order to utilize the porous coating implant in this process. Next, the process moves to block 910. There, the soft tissue is returned to the bone and over the coated implant so that the healing process may begin.

Figure 10:
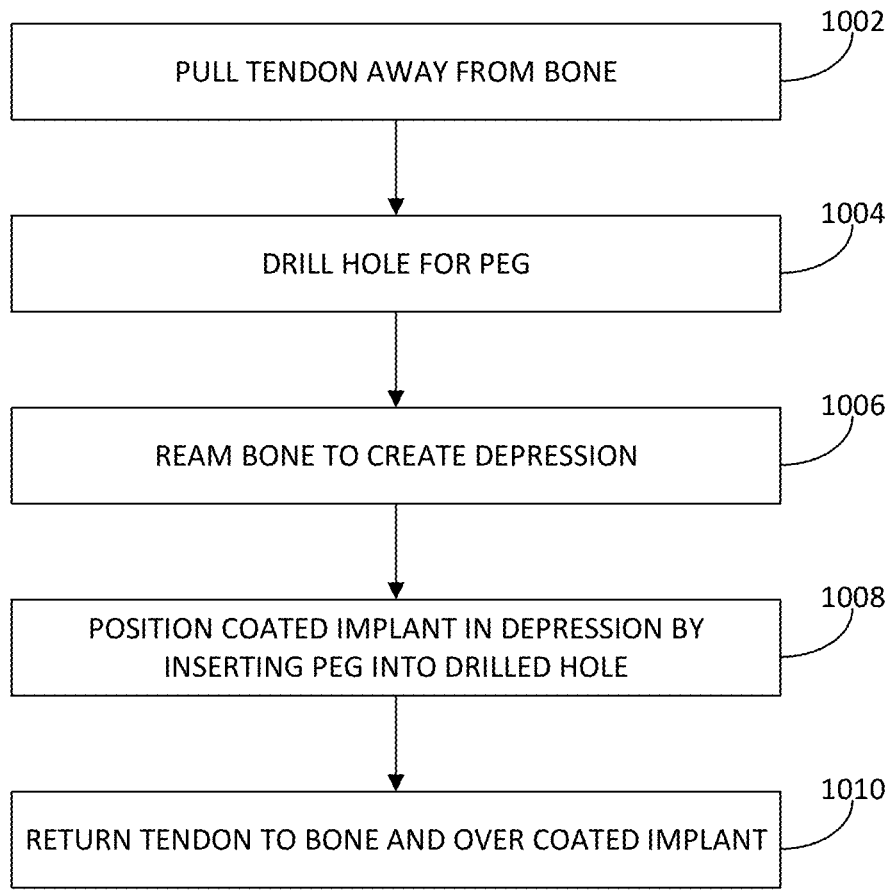
FIG. 10 is an example of another suture-less method of repairing soft tissue using a porous coating implant.

In some embodiments, the porous coating implant may include a stem such as a peg (as shown in FIGS. 1A-1E) and a threaded post (as shown in FIGS. 2A-2E). FIG. 10 is an example of another suture-less method of repairing soft tissue using a porous coating implant having a stem portion. The process begins at block 1002, where the tendon and/or other soft tissue is pulled away from the bone to expose the placement location for the implant. The process then moves to block 1004, where a hole is drilled to receive the stem portion of the porous coating implant. Next, the process moves to block 1006 where a depression is made in the bone surrounding the drilled hole using a reamer or some other surgical tool. The process next moves to block 1008. There, the porous coating implant is positioned in the form depression by inserting its stem into the drilled hole. If the stem is a non-threaded stem, the implant may be press fit into the drilled hole. If the stem is a threaded stem, it may be inserted into the drill hole rotationally, using some form of rotational driving tool. Once the coated implant is properly positioned, the process then moves to block 1010 where the soft tissue and/or tendon may then be returned to the bone and placed over the coated implant to allow the healing process to begin.

Figure 11A:
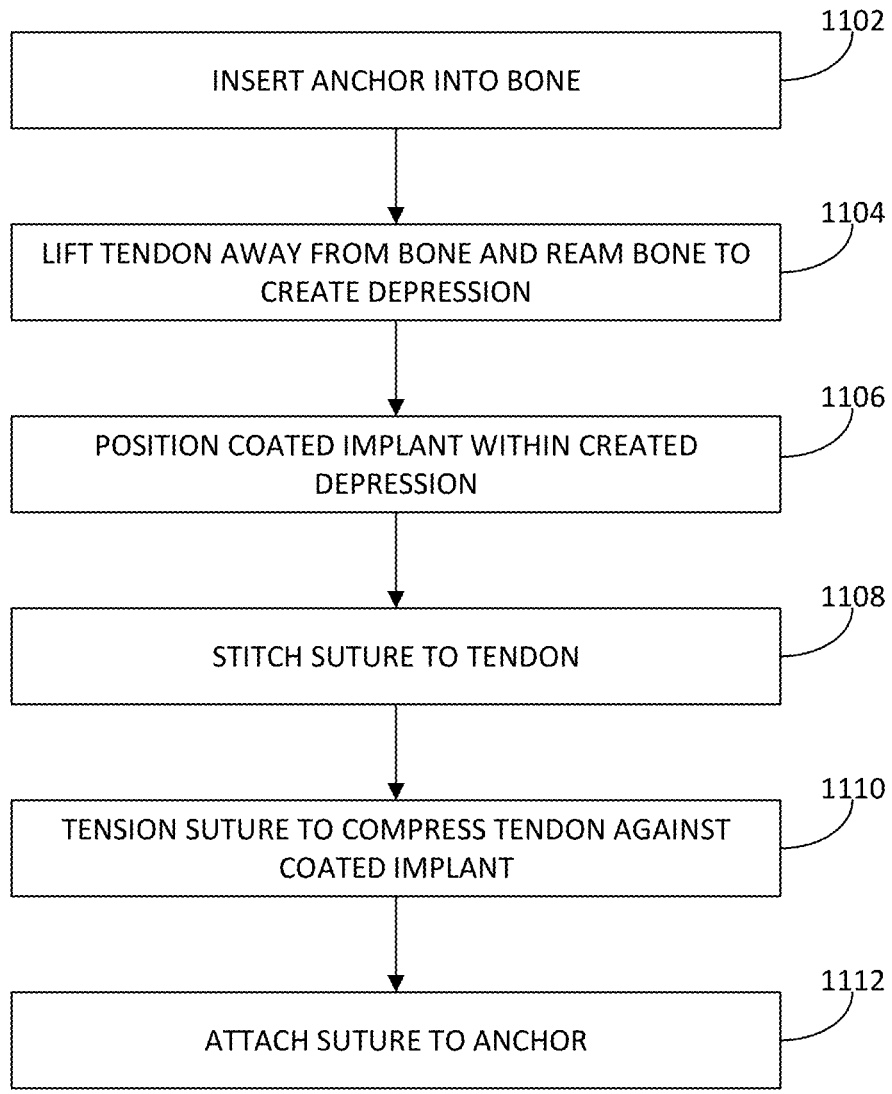
FIG. 11A is an example of an enhanced single row soft tissue repair method according to one or more embodiments.

The porous coating implants disclosed herein may also be utilized to supplement and enhance traditional soft tissue repair constructs. FIG. 11A is an example of an enhanced single row soft tissue repair method according to one or more embodiments. The process begins with an anchor being inserted into the patient's bone at block 1102. The process then moves to block 1104 where the tendon and/or soft tissue is lifted away from the bone, and the bone is reamed in order to form a slight depression in the bone outer surface. Next, the process moves to block 1106 where a porous coating implant is positioned within the form depression. The process next moves to block 1108, where a suture is stitched to the tendon and/or soft tissue. Next, the suture is tensioned to compress the tendon and/or soft tissue against the porous coating implant at block 1110. Once the tendon and/or soft tissue has been compressed against the coated implant, the suture is then attached to the bone anchor. The suture may be attached to the bone anchor using a knot tying technique, or alternatively using a knotless anchor which requires no knot tying.

Figure 11B:
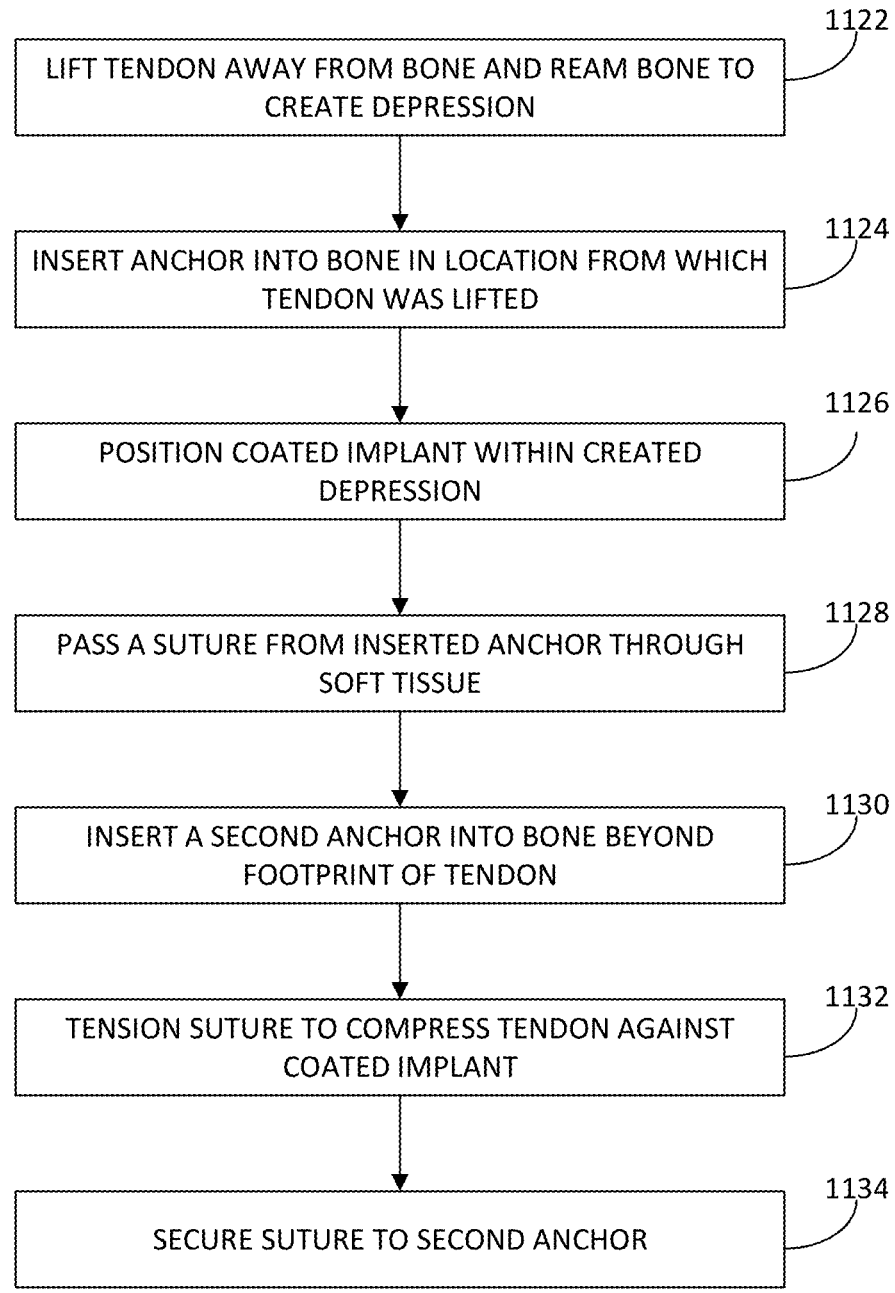
FIG. 11B is an example of an enhanced double row soft tissue repair method according to one or more embodiments.

The porous coating implants disclosed herein may also be used to improve double row soft tissue repair procedures. FIG. 11B is an example of an enhanced double row soft tissue repair method according to one or more embodiments. The process begins at block 1122, where the injured tendon and/or soft tissue is lifted away from the bone in the bone is reamed in order to form a slight depression in the surface of the bone. Next, the process moves to block 1124, wherein anchor is inserted into the bone in or around the location from which the tendon was lifted. Next the process moves to block 1126 where the porous coating implant is positioned within the created depression. The porous coating implant may be positioned within the created depression in various ways as discussed above including press fitting, tamping, screwing/rotating, or some other positioning technique. Next, the process moves to block 1128, where a suture is passed from the inserted anchor through the soft tissue. The suture may be pre-attached to the inserted anchor, and it may be passed upwardly and out through the bottom surface of the soft tissue. The process may then move to block 1130, where a second anchor may be inserted into the bone beyond the footprint of the tendon and/or soft tissue. Thus, the second anchor may be inserted outside the original footprint of the tendon and not underneath the tendon like the first anchor. Next, the process moves to block 1132 where the suture may be tensioned in order to compress the tendon and/or soft tissue against the porous coating implant which is positioned underneath the tendon and/or soft tissue. Once the tendon and/or soft tissue is compressed against the porous coating implant, the suture may be then secured to the second anchor, thereby creating a soft tissue repair construct in which the sutures to hold the repaired tendon in place and against the porous coating implant.

Although has been described with reference to embodiments and examples, it should be understood that numerous in various modifications can be made without departing from the spirit of the invention. Accordingly, the invention is limited only by the following claims.

What is claimed is:

1. A method of attaching a soft tissue to a bone, the method comprising:
    forming a depression in the bone underneath an anatomical footprint of the soft tissue;
    positioning an implant within the depression, the implant comprising:
        an implant frame having a plurality of apertures arranged in concentric circles around a central aperture, and
        a porous coating disposed over the implant frame and extending through the plurality of apertures and the central aperture; and
    compressing the soft tissue against the implant.

2. The method of claim 1, wherein the implant provides both bone in-growth and soft tissue in-growth.

3. The method of claim 1, further comprising, prior to forming the depression in the bone, lifting the soft tissue away from the bone to expose a surface of the bone.

4. The method of claim 3, wherein forming the depression in the bone comprises reaming the surface of the bone to create the depression in a cortical shell of the bone.

5. The method of claim 4, wherein the depression has a substantially circular shape.

6. The method of claim 5, wherein the implant has a substantially circular shape, and wherein the implant fits within the depression in the bone.

7. The method of claim 5, further comprising securing the implant within the depression.

8. The method of claim 7, wherein the implant comprises at least one eyelet.

9. The method of claim 8, wherein securing the implant comprises inserting a fixation device through the at least one eyelet to penetrate the bone.

10. The method of claim 9, wherein the soft tissue is compressed against the implant without the use of any suture material.

11. The method of claim 1, wherein the porous coating comprises a porous titanium coating.

12. The method of claim 11, wherein the porous titanium coating comprises a first distinct pore size and a second distinct pore size.

13. The method of claim 12, wherein the first distinct pore size promotes integration with the soft tissue.

14. The method of claim 12, wherein the second distinct pore size promotes integration with bone.

15. The method of claim 12, wherein at least a portion of the implant frame remains uncoated by the porous coating after application of the porous coating.

16. A method of attaching soft tissue to a bone, the method comprising:
    inserting an anchor into the bone;
    lifting soft tissue away from the bone;
    positioning an implant on a bone surface underneath an anatomical footprint of the soft tissue, the implant comprising:
        an implant frame having a plurality of apertures arranged in concentric circles around a central aperture, and
        a porous coating disposed over the implant frame and extending through the plurality of apertures and the central aperture;
    stitching a suture to the soft tissue;
    tensioning the suture to compress the soft tissue against the implant; and
    attaching the suture to the inserted anchor.

17. A method of attaching soft tissue to a bone, the method comprising:
    lifting the soft tissue away from the bone;
    inserting a first bone anchor into the bone underneath an anatomical footprint of the soft tissue;
    positioning an implant on a surface of the bone underneath the anatomical footprint of the soft tissue, the implant comprising:
        an implant frame having a plurality of apertures arranged in concentric circles around a central aperture, and
        a porous coating disposed over the implant frame and extending through the plurality of apertures and the central aperture;
    passing a suture from the first bone anchor through the soft tissue;

inserting a second bone anchor into the bone, beyond the anatomical footprint of the soft tissue;

tensioning the suture to compress the soft tissue against the implant and the bone; and securing the tensioned suture to the second bone anchor.

* * * * *